United States Patent
Ishiguro et al.

(10) Patent No.: US 7,868,183 B2
(45) Date of Patent: Jan. 11, 2011

(54) PROCESS FOR PRODUCING MUSCARINE RECEPTOR ANTAGONIST AND INTERMEDIATE THEREFOR

(75) Inventors: Yuuji Ishiguro, Saitama (JP); Yasuhiro Aizawa, Kitaazumino-gun (JP); Masahiro Aono, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 377 days.

(21) Appl. No.: 11/721,378

(22) PCT Filed: Dec. 13, 2005

(86) PCT No.: PCT/JP2005/023216

§ 371 (c)(1),
(2), (4) Date: Feb. 7, 2008

(87) PCT Pub. No.: WO2006/064945

PCT Pub. Date: Jun. 22, 2006

(65) Prior Publication Data

US 2009/0299075 A1     Dec. 3, 2009

(30) Foreign Application Priority Data

Dec. 14, 2004   (JP)   .............................. 2004-361243

(51) Int. Cl.
    *C07D 233/64*     (2006.01)
(52) U.S. Cl. .................................................. 548/338.1
(58) Field of Classification Search ................ 548/338.1
    See application file for complete search history.

(56) References Cited

U.S. PATENT DOCUMENTS

| 5,932,607 A | * | 8/1999 | Miyachi et al. ............. 514/399 |
| 6,350,880 B1 | | 2/2002 | Tadashi et al. |

FOREIGN PATENT DOCUMENTS

| EP | 0 733 621 | 9/1996 |
| JP | 7 291936 | 11/1995 |
| JP | 2003 201281 | 7/2003 |
| WO | 95 15951 | 6/1995 |

OTHER PUBLICATIONS

Vippagunta et al., Crystalline solids, 2001, Advanced Drug Delivery Reviews, 48, pp. 3 and 18.*

Miyachi, H. et al., "Synthesis and Antimuscarinic Activity of a Series of 4(1-Imidazolyl)-2,2-Diphenylbutyramides: Discovery of Potent and Subtype-Selective Antimuscarinic Aents" Bioorganic and Medicinal Chemistry, Elsevier Science Ltd., GB, vol. 7, No. 6, Jun. 1, 1999, pp. 1151-1161.

Armarego, W. L. F., et al., "Purification of Laboratory Chemicals (Fifth Edition)", 2003, Elsevier Butterworth-Heinemann, XP002511132, p. 63.

* cited by examiner

*Primary Examiner*—Kamal A Saeed
*Assistant Examiner*—Kristin Bianchi
(74) *Attorney, Agent, or Firm*—Oblon, Spivak, McClelland, Maier & Neustadt, L.L.P.

(57) ABSTRACT

The industrial production of 4-(2-methyl-1-imidazolyl)-2,2-diphenylbutanamide, a urinary incontinence remedy, necessitates elimination of problems concerning the use of a synthetic adsorbent, e.g., HP-20, the efficiency of operation with the same, purification efficiency, etc. An acid salt, e.g., hydrochloride or phosphate, of 4-(2-methyl-1-imidazolyl)-2,2-diphenylbutanamide or a hydrate of any of these salts is used as an intermediate. This intermediate is neutralized and then purified. Thus, high-purity 4-(2-methyl-1-imidazolyl)-2,2-diphenylbutanamide is easily obtained in satisfactory yield. The industrial-scale production process has been thus established.

11 Claims, No Drawings

PROCESS FOR PRODUCING MUSCARINE RECEPTOR ANTAGONIST AND INTERMEDIATE THEREFOR

TECHNICAL FIELD

The present invention relates to a novel preparative intermediate of 4-(2-methyl-1-imidazolyl)-2,2-diphenylbutanamide (hereinafter abbreviated as "Compound (1)") being a selective muscarinic receptor antagonist, and a preparative process of Compound (1) using that intermediate.

BACKGROUND TECHNOLOGY

Compound (1)

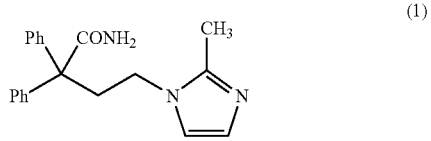

is an imidazole derivative having anticholinergic effect, above all, selective and potent antagonistic function against muscarine receptor, and it is known that it is useful for medicinal uses for the therapies of motility disorders in digestive tract such as irritative colon syndrome, diverticulosis, functional diarrhea, esophageal achalasia and cardiospasm, therapies of convulsion of biliary tract or urinary tract and incontinence of urine, etc., and therapy of chronic respiratory tract-obstructive disease, and the like (compounds of Patent document 1 and Example 11 of Patent document 2). Also, the preparative processes of Compound (1) are disclosed concretely (Patent documents 2 and 3, Nonpatent document 1). However, in the processes disclosed therein, synthetic adsorbent such as HP-20 must be used on purification, which has problems on the operativities, purification efficiencies, etc. from the viewpoint of intending industrial scale-up. Hence, there has been a necessity for further improvement and contrivance to find out a preparative process that adapts to the practical production.

[Patent document 1] WO9515951 pamphlet
[Patent document 2] Jpn. Kokai Tokkyo Koho JP 007,215,943
[Patent document 3] Jpn. Kokai Tokkyo Koho JP 2003-201281
[Nonpatent document 1] Bioorg. Med. Chem., 7 (6), 1151-1161 (1999).

DISCLOSURE OF THE INVENTION

For keeping the industrial production of high-quality Compound (1) as a medicinal drug, it is necessary to solve the problems of improvements in the operability and purification efficiency in the preparative process that adapt to practical production level, or the problems of possibility of the synthetic adsorbent being mixed into the original drug.

As a result of diligent studies for solving the problems aforementioned, the inventors have found that, by separating and purifying salt of hydrochloride, phosphate or the like of 4-(2-methyl-1-imidazolyl)-2,2-diphenylbutanamide, or hydrate of that salt, as a preparative intermediate, and then, by neutralizing, Compound (1) can be prepared by simple operation and with good purification efficiency, leading to the completion of the invention.

Namely, the invention relates to 1) salt of 4-(2-methyl-1-imidazolyl)-2,2-diphenylbutanamide, or hydrate of that salt, 2) hydrochloride or phosphate of 4-(2-methyl-1-imidazolyl)-2,2-diphenylbutanamide, or hydrate of that acid salt, 3) acid salt or hydrate of that acid salt of said 2), characterized in that it is a preparative intermediate of 4-(2-methyl-1-imidazolyl)-2,2-diphenylbutanamide, 4) acid salt or hydrate of that acid salt of said 2), characterized in that it is a preparative intermediate for preparing purified product of 4-(2-methyl-1-imidazolyl)-2,2-Diphenylbutanamide, which is easy for isolation and purification, 5) a process for preparing isolated and purified product of acid salt or hydrate of that acid salt of said 2), wherein inorganic acid or organic acid is reacted with crude crystals of 4-(2-methyl-1-imidazolyl)-2,2-diphenylbutanamide to isolate and purify the acid salt or hydrate of that acid salt, 6) a process for preparing purified 4-(2-methyl-1-imidazolyl)-2,2-diphenylbutanamide by neutralizing the isolated and purified product of acid salt or hydrate of that acid salt of said 5) with alkali, 7) a process for preparing purified product of 4-(2-methyl-1-imidazolyl)-2,2-diphenylbutanamide, wherein the acid salt of 4-(2-methyl-1-imidazolyl)-2,2-diphenylbutanamide, or hydrate of that acid salt isolated in said 5) is recrystallized from alcohol and ethyl acetate, followed by neutralization, by using hydroxide of alkali metal, and the crystals obtained are recrystallized from alcohol or water-containing alcohol, and 8) the acid salt or hydrate of that acid salt of said 2) or 3), that is possible to provide 4-(2-methyl-1-imidazolyl)-2,2-diphenylbutanamide with high quality in good yield only by simple recrystallization.

According to the invention, a preparative process for 4-(2-methyl-1-imidazolyl)-2,2-diphenylbutanamide that is advantageous industrially is established and it is possible to provide it as a high-purity and high-quality medicinal drug.

BEST MODE FOR CARRYING OUT THE INVENTION

The salt of 4-(2-methyl-1-imidazolyl)-2,2-diphenylbutanamide means addition salt with inorganic acid such as hydrochloric acid, sulfuric acid, hydrobromic acid or phosphoric acid, or addition salt with organic acid such as maleic acid, fumaric acid, acetic acid, oxalic acid, tartaric acid or benzenesulfonic acid. Thereamong, hydrochloride or phosphate is preferable.

In the invention, crude crystals 4-(2-methyl-1-imidazolyl)-2,2-diphenylbutanamide are obtained according to Patent document 3, these are dissolved into alcohol such as methanol, ethanol, propanol or 2-propanol, equimolar acid such as hydrochloric phosphoric acid is added, then, organic solvent such as ethyl acetate is added, or crystallization is made by using an equimolar mixed solution of acid such as hydrochloric acid or phosphoric acid, alcohol and ethyl acetate, thereby isolating 4-(2-methyl-1-imidazolyl)-2,2-diphenylbutanamide as an acid salt of hydrochloride, phosphate or the like, or hydrate thereof, and then, after neutralization by using alkali metal hydroxide, it is recrystallized from alcohol such as methanol ethanol, propanol or 2-propanol or water-containing alcohol thereof. Through these steps, it has been found that Compound (1) with high-purity can be obtained by simple operation and in good purification efficiency, leading to the completion of industrial scale preparative process (scheme).

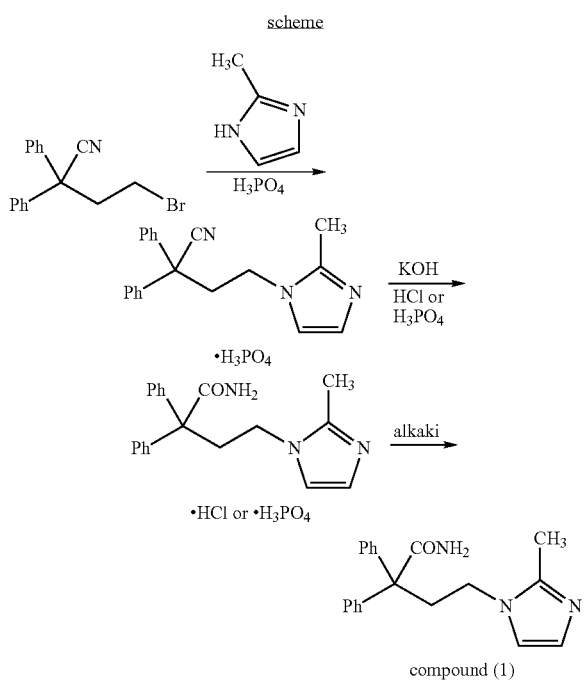

scheme compound (1)

The inventive acid salt of hydrochloride, phosphate or the like of 4-(2-methyl-1-imidazolyl)-2,2-diphenylbutanamide, or hydrate of that salt is a novel compound with no concrete disclosure, and its usefulness has also been unknown. By using this novel salt or hydrate of that salt, it has been found that the purification efficiency improves and the purifying operation also becomes simple, thereby completing the invention as an industrial process.

If using the inventive acid salt of hydrochloride, phosphate or the like of 4-(2-methyl-1-imidazolyl)-2,2-diphenylbutanamide, or hydrate of that salt, then original drug of high-quality Compound (1) can be obtained in good yield, only by simple recrystallization of crude product without using synthetic adsorbent. According to the invention, excellent industrial production process of Compound (1) has been provided.

EXAMPLE

In following, the invention will be illustrated based on concrete examples, but the invention is not confined to these examples.

Referential Example 1

Crude Crystals of 4-(2-methylimidazole-1-yl)-2,2-diphenylbutanamide

A mixture of 500 g (1.67 mol) of 4-bromo-2,2-diphenylbutyronitrile, 685 g (8.34 mol) of 2-methylimidazole and 250 mL of dimethylsulfoxide (DMSO) was stirred for 5 hours at 95 to 105° C., and then cooled with ice water. After 2 L of ethyl acetate and 2 L of water were added therein at an inner temperature of 39° C., and the mixture was stirred for 5 minutes, organic layer was separated. After washing the organic layer with 2 L of water and then 2 L of 2.5% acetic acid, the organic layer was concentrated under reduced pressure. The residual oil was dissolved in 2 L of ethanol and to this solution a solution of 192 g (1.67 mol) of 85% phosphoric acid and 1 L of ethanol was added dropwise at an inner temperature of 31° C. under stirring, and this dropwise addition was interrupted when the solution became milky white (about 500 mL were added dropwise). After confirming the precipitation of crystals by stirring for 30 minutes, remaining phosphoric acid solution was added dropwise, and successively the solution was stirred for 16 hours at an inner temperature of 30° C. The precipitated crystals were collected by filtration and, after washing them with 1 L of ethanol, the crystals were dried for 5 hours at 60° C. under reduced pressure (vacuum pump) to obtain 496 g (74.5%) of 4-(2-methylimidazole-1-yl)-2,2-diphenylbutyronitrile phosphate. Out of these crystals, 100 g were completely dissolved with stirring into a mixture of 100 mL of purified water and 400 mL of 2-propanol and to this solution 500 mL of 2-propanol were added under stirring, followed by cooling with ice water. After stirring this solution for 1 hour at an inner temperature of below 15° C., the precipitated crystals were collected by filtration which were then washed with 100 mL of 2-propanol, then with 100 mL of ethyl acetate. The crystals were dried for 17 hours at 60° C. under reduced pressure (vacuum pump) to obtain 91.3 g (Total yield: 68%) of purified product of 4-(2-methylimidazole-1-yl)-2,2-diphenylbutyronitrile phosphate as white crystalline powder with hygroscopicity. After a mixture of 80.0 g (200 mmol) of the purified product thus obtained, 132 g (2.02 mol) of 86% potassium hydroxide and 400 ml of 2-propanol was refluxed for 5 hours under an atmosphere of argon, the mixture was cooled with ice water. Under stirring, 800 mL of 2 mol/L hydrochloric acid were added into the mixture at an inner temperature of 30° C. (temperature was raised to 50° C.) to crystallize out of the mixture, and, after stirring for 1 hour at an inner temperature of below 15° C., the crystals were collected from the solution by filtration. These crystals were washed with a mixture of 30 mL of 2-propanol and 60 mL of purified water, then with each 250 mL of purified water five times (fifth washed solution: pH 8.80). The crystals were dried for 16 hours at 40° C. in blower to obtain 55.2 g (86.4%) of crude crystals. Into a mixed solution of 200 mL of 95% 2-propanol, 27.6 g out of these were dissolved completely by heating, which was then stirred for 1 hour at room temperature to crystallize out of the solution, followed by cooling with ice water. After stirring the solution for 1 hour at an inner temperature of below 15° C., the precipitated crystals were collected by filtration and washed with 10 mL of 2-propanol. The crystals were dried for 3 hours at 60° C. under reduced pressure (vacuum pump) to obtain 25.7 g (Total yield: 80%) of crude crystals of 4-(2-methylimidazole-1-yl)-2,2-diphenylbutanamide as white crystalline powder.

Example 1

4-(2-Methyl-1-imidazolyl)-2,2-diphenylbutanamide hydrochloride

Into a mixed solution of 5 mL of concentrated hydrochloric acid/95 mL of 2-propanol, 19.2 g (60.0 mmol) of crude crystals of 4-(2-methyl-1-imidazolyl)-2,2-diphenylbutanamide obtained in Referential example 1 were dissolved completely by heating, then 100 mL of ethyl acetate were added into the solution, and it was stirred for 1 hour at room temperature to crystallize out of the solution, followed by cooling with ice water. After stirring it for 1 hour at an inner temperature of below 15° C., the crystals were collected by filtration and washed with 10 mL of ethyl acetate. After completely dissolving the wet crystals into 100 mL of 95% 2-propanol by heating, 100 mL of ethyl acetate were added into the solution, and it was stirred for 1 hour at room temperature to crystallize out of the solution, followed by cooling with ice water. After stirring it for 1 hour at an inner temperature of below 15° C., the crystals were collected by filtration and washed with 10 mL of ethyl acetate. The crystals were dried for 3 hours at 60° C. under reduced pressure (vacuum pump) to obtain 16.9 g (79.3%) of 4-(2-methyl-1-imidazolyl)-2,2-diphenylbutanamide hydrochloride. After completely dissolving this hydrochloride into 80 mL of 90% 2-propanol by heating, 160 mL of ethyl acetate were added into the solution, and it was stirred for 1 hour at room temperature to crystallize out of the solution, followed by cooling with ice water. After stirring for 1 hour at an inner temperature of below 15° C., the crystals were collected by filtration and washed with 10 mL of ethyl acetate. The crystals were dried for 3 hours at 60° C. under reduced pressure (vacuum pump) to obtain 14.5 g (Total yield: 68%) of 4-(2-methyl-1-imidazolyl)-2,2-diphenylbutanamide hydrochloride as white crystalline powder.

mp 205-208° C. (Hot plate method) EI-MS m/z: 319 ($M^+$) Anal. Calcd. $C_{20}H_{21}N_3O \cdot HCl$: C, 67.50; H, 6.23; N, 11.81. Found: C, 67.25; H, 6.26; N, 11.83.

$^1$H-NMR (DMSO-$d_6$, 400 MHz) δ: 2.38 (3H, s), 2.75-2.79 (2H, m), 3.73-3.77 (2H, m), 6.81 (1H, s), 7.28-7.39 (10H, m), 7.44 (1H, s), 7.50 (1H, d, J=2.4 Hz), 7.55 (1H, d, J=2.0 Hz), 14.41 (1H, br s).

Example 2

4-(2-methyl-1-imidazolyl)-2,2-diphenylbutanamide

In 71 mL of purified water, 7.12 g (20.0 mmol) of 4-(2-methyl-1-imidazolyl)-2,2-diphenylbutanamide hydrochloride obtained in Example 1 were dissolved and 0.71 g of activated charcoal were added into the solution. After stirring it for 1 hour, the mixture was filtered through 2.1 cm-size Kiriyama funnel laid with 1.00 g of cellulose powder and washed with 3 mL of purified water. To the filtrate and washed solution, 56 mL of ethanol were added, and, under stirring, 10 mL of 2 mol/L sodium hydroxide solution were added into the solution to neutralize and crystallize out of the solution. The suspension was stirred for 1 hour at room temperature and then cooled with ice water. After stirring it for 1 hour at an inner temperature of below 15° C., the crystals were collected by filtration and washed with 10 mL of 40% ethanol, then with each 100 mL of purified water five times (fifth washed solution: pH 8.57). The crystals were dried for 5 hours at 60° C. under reduced pressure (vacuum pump) to obtain 5.88 g (92.0%) of crystals. Into 30 mL of 90% ethanol, 5.78 g out of these were dissolved completely by heating, which was stirred for 1 hour at room temperature to crystallize out of solution, followed by cooling it with ice water. After stirring it for 1 hour at an inner temperature of below 15° C., the crystals were collected by filtration and washed with 5 mL of ethanol. The crystals were dried for 3 hours at 60° C. under reduced pressure (vacuum pump) to obtain 5.22 g (Total yield: 83%) of 4-(2-methyl-1-imidazolyl)-2,2-diphenylbutanamide as white crystalline powder.

mp 191-193° C. (Hot plate method) EI-MS m/z: 319 ($M^+$) IR (KBr) $cm^{-1}$: 3333, 3047, 1673, 1499. Anal. Calcd. $C_{20}H_{21}N_3O$: C, 75.21; H, 6.63; N, 13.16. Found: C, 75.34; H, 6.66; N, 13.37.

$^1$H-NMR (DMSO-$d_6$, 400 MHz) δ: 2.01 (3H, s), 2.60-2.64 (2H, m), 3.51-3.55 (2H, m), 6.67 (1H, d, J=1.2 Hz), 6.90 (1H, brs), 6.92 (1H, d, J=1.2 Hz), 7.25-7.37 (11H, m).

[Conditions for Measuring HPLC]

Detector: An ultraviolet absorption photometer (wavelength: 227 nm.

Column: A stainless steel column of 4.6 mm in inside diameter and 15 cm in length, packed with octadecylsilanized silicagel for liquid chromatography, 5 μm in particle diameter (Inertsil ODS-3V).

Column Temperature: A constant temperature of about 30° C.

Mobile Phase A: Dissolved 2.16 g of sodium 1-octanesulfonate in diluted phosphoric acid (1 in 1000) to make 1000 mL. Mobile phase B: Acetonitrile. Mobile phase C: Methanol. During 40 minutes after injection of sample, feeding was controlled on linear concentration gradient from mixed solution of mobile phase A/mobile phase B/mobile phase C (12:5:3) to mixed solution of mobile phase B/mobile phase A/mobile phase C (12:5:3), and during next 10 minutes, mixed solution of mobile phase B/mobile phase A/mobile phase C (12:5:3) was fed.

Flow Rate: This was adjusted so as the retention time of KRP-197 to become 9 to 10 minutes (ca. 1 mL/min).

Time Span of Measurement: about 5 times as long as the retention time of KRP-197 (about 45 minutes).

HPLC Purity: 100%.

Example 3

4-(2-Methyl-1-imidazolyl)-2,2-diphenylbutanamide phosphate

Into 11 times volume of 90% 2-propanol, crude crystals of 4-(2-methyl-1-imidazolyl)-2,2-diphenylbutanamide obtained similarly to Referential example 1 were dissolved by heating. After equimolar 85% phosphoric acid was added, the precipitated insolubles were dissolved by heating, and the solution was stirred for 1 hour at room temperature, then for 1 hour under cooling with ice water to make phosphate crystals, followed by filtration. After drying, these were recrystallized from ten times volume 70% 2-propanol. The crystals were dried for 3 hours at 60° C. under reduced pressure (vacuum pump) to obtain 37.3 g (sum-up yield: 89%) of 4-(2-methyl-1-imidazolyl)-2,2-diphenylbutanamide phosphate.

mp 219-220° C. (Hot plate method) EI-MS m/z: 319 ($M^+$) Anal. Calcd. $C_{20}H_{21}N_3O \cdot H_3PO_4 \cdot 0.8H_2O$: C, 55.63; H, 5.98; N, 9.73. Found: C, 55.52; H, 5.82; N, 9.69.

$^1$H-NMR (DMSO-$d_6$, 400 MHz) δ: 2.13 (3H, s), 2.65-2.69 (2H, m), 3.58-3.62 (2H, m), 6.87 (1H, brs), 6.90 (1H, d, J=1.5 Hz), 7.10 (1H, d, J=1.5 Hz), 7.26-7.43 (11H, m), 8.41 (2H, br).

Example 4

4-(2-Methyl-1-imidazolyl)-2,2-diphenylbutanamide

Into a mixture of 32 mL of 1 mol/L hydrochloric acid and 101 mL of purified water, 13.3 g (32.0 mmol) of 4-(2-methyl-1-imidazolyl)-2,2-diphenylbutanamide phosphate obtained in Example 3 were dissolved, and 1.33 g of activated charcoal were added. After stirring for 1 hour, the mixture was filtered through 4 cm-size Kiriyama funnel, in which 2.66 g of cellulose powder was laid and washed with 13 mL of purified water. To the filtrate and washed solutions 130 mL of ethanol were added, and, under stirrings 48 mL of 2 mol/L sodium hydroxide solution were added to neutralize the solution and crystallize out of the solution. After stirring for 1 hour at an inner temperature of below 15° C. under cooling with ice water, the crystals were collected by filtration and washed with 50 mL of 40% ethanol, then with each 200 mL of purified water five times (fifth washed solution: pH 8.80). Into 53 mL of ethanol, 10.6 g of wet crystals were dissolved completely by heating, and the solution was stirred for 1 hour at room temperature to crystallize out of the solution, followed by cooling with ice water. After stirring for 1 hour at an inner temperature of below 15° C., the crystals were collected by filtration and washed with 5 mL of ethanol. The crystals were dried for 3 hours at 60° C. under reduced pressure (vacuum pump) to obtain 7.80 g (yield: 76.3%) of 4-(2-methyl-1-imidazolyl)-2,2-diphenylbutanamide as white crystalline powder.

HPLC Purity: 100%.

INDUSTRIAL APPLICABILITY

Upon preparing 4-(2-methyl-1-imidazolyl)-2,2-diphenylbutanamide, it has become clear that, by separating 4-(2-methyl-1-imidazolyl)-2,2-diphenylbutanamide as an acid salt of hydrochloride phosphate or the like, or hydrate thereof, being an intermediate, followed by purification, then, by neutralizing with alkali metal hydroxide and recrystallizing using alcohol, high-quality 4-(2-methyl-1-imidazolyl)-2,2-diphenylbutanamide can be provided in good efficiency.

According to the invention, industrially advantageous preparative process of 4-(2-methyl-1-imidazolyl)-2,2-diphenylbutanamide has been established, thereby making it possible to provide it as a high-purity and high-quality medicinal drug.

The invention claimed is:

1. A process for preparing purified 4-(2-methyl-1-imidazolyl)-2,2-diphenylbutanamide by neutralizing a salt of 4-(2-methyl-1-imidazolyl)-2,2-diphenylbutanamide with alkali.

2. A process for preparing purified 4-(2-methyl-1-imidazolyl)-2,2-diphenylbutanamide, the method comprising
  recrystallizing a salt of 4-(2-methyl-1-imidazolyl)-2,2-diphenylbutanamide from alcohol and ethyl acetate,
  neutralizing the recrystallized salt with an alkali metal hydroxide to obtain crystals, and
  recrystallizing the crystals from alcohol or water-containing alcohol.

3. The process according to claim 1, wherein the salt of 4-(2-methyl-1-imidazolyl)-2,2-diphenylbutanamide is a hydrochloride salt.

4. The process according to claim 1, wherein the salt of 4-(2-methyl-1-imidazolyl)-2,2-diphenylbutanamide is a phosphate salt.

5. The process according to claim 2, wherein the salt of 4-(2-methyl-1-imidazolyl)-2,2-diphenylbutanamide is a hydrochloride salt.

6. The process according to claim 2, wherein the salt of 4-(2-methyl-1-imidazolyl)-2,2-diphenylbutanamide is a phosphate salt.

7. The process according to claim 2, wherein the alcohol is methanol, ethanol, propanol or 2-propanol.

8. The process according to claim 2, further comprising
  isolating an acid salt of 4-(2-methyl-1-imidazolyl)-2,2-diphenylbutanamide generated by adding an inorganic acid or organic acid to a crude crystal of the salt of 4-(2-methyl-1-imidazolyl)-2,2-diphenylbutanamide followed by recrystallizing the acid salt from alcohol and ethyl acetate;
  treating the acid salt of 4-(2-methyl-1-imidazolyl)-2,2-diphenylbutanamide obtained by the recrystallizing with an active carbon; and
  neutralizing the acid salt of 4-(2-methyl-1-imidazolyl)-2,2-diphenylbutanamide obtained from the treating with active carbon with an alkali metal hydroxide followed by recrystallizing the material obtained after neutralizing from alcohol or water-containing alcohol.

9. The process according to claim 8, wherein the 4-(2-methyl-1-imidazolyl)-2,2-diphenylbutanamide salt after conducing the isolating, recrystallization, treating, neutralizing and recrystallizing has a HPLC purity of 100%.

10. The process according to claim 2, further comprising
  isolating the acid salt of 4-(2-methyl-1-imidazolyl)-2,2-diphenylbutanamide by adding hydrochloric acid or phosphoric acid to a crude crystal of 4-(2-methyl-1-imidazolyl)-2,2-diphenylbutanamide followed by recrystallizing the acid salt from 95% 2-propanol and ethyl acetate;
  treating the acid salt of 4-(2-methyl-1-imidazolyl)-2,2-diphenylbutanamide obtained from the recrystallizing with an active carbon; and
  neutralizing the acid salt of 4-(2-methyl-1-imidazolyl)-2,2-diphenylbutanamide obtained after the treating with active carbon with an alkali metal hydroxide, followed by recrystallizing the material obtained after neutralizing from alcohol or water-containing alcohol.

11. The process according to claim 10, wherein the 4-(2-methyl-1-imidazolyl)-2,2-diphenylbutanamide salt after conducing the isolating, recrystallization, treating, neutralizing and recrystallizing has a HPLC purity of 100%.

* * * * *